United States Patent
Kohler

(10) Patent No.: US 6,641,600 B1
(45) Date of Patent: *Nov. 4, 2003

(54) PROCESS AND APPARATUS FOR THE COSMETIC TREATMENT OF ACNE VULGARIS

(75) Inventor: Wolfgang Kohler, Schnaittach (DE)

(73) Assignee: SLI Lichtsysteme GmbH, Erlangen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/857,452
(22) PCT Filed: Dec. 4, 1998
(86) PCT No.: PCT/EP98/07884
§ 371 (c)(1), (2), (4) Date: Jun. 4, 2001
(87) PCT Pub. No.: WO00/32272
PCT Pub. Date: Jun. 8, 2000

Related U.S. Application Data

(63) Continuation of application No. 09/204,593, filed on Dec. 3, 1998, now Pat. No. 6,183,500.

(51) Int. Cl.⁷ .................................................. A61N 5/06
(52) U.S. Cl. ............................ 607/90; 128/898; 607/88
(58) Field of Search ...................... 606/2–18; 607/88–94

(56) References Cited

U.S. PATENT DOCUMENTS

| | | | |
|---|---|---|---|
| 4,599,536 A | * | 7/1986 | Steeger et al. ............... 313/493 |
| 4,930,504 A | | 6/1990 | Diamantopoulos et al. |
| 5,549,660 A | | 8/1996 | Mendes et al. |
| 5,610,477 A | * | 3/1997 | Ivanov et al. ............... 313/573 |
| 6,183,500 B1 | | 2/2001 | Köhler |

FOREIGN PATENT DOCUMENTS

| | | |
|---|---|---|
| DE | 19724299 | 12/1998 |
| GB | 2190994 | 12/1987 |
| WO | WO 9614899 | 5/1996 |

OTHER PUBLICATIONS

Article: "Aknetherapie mit sichtbarem Licht" ("Acne Treatment With Visible Light"), p. 597–603 (See the English language summary of the article in the middle of p. 597–first page).

Wallace, Trudi, "Could a beam of light reduce the lines on your face?" Daily Mail, Jun. 11, 1998, pp. 44–45.

Halle, Martyn, "A lamp to treat acne in safety," Daily Mail, May 12, 1998, p. 43.

* cited by examiner

*Primary Examiner*—Lee Cohen
*Assistant Examiner*—Henry M. Johnson, III
(74) *Attorney, Agent, or Firm*—Brooks Kushman P.C.

(57) ABSTRACT

A process and apparatus for the cosmetic treatment of acne vulgaris utilize irradiation of the affected skin areas with light characterized by a combination of two emission spectra, one in a blue region and the other in a red region.

26 Claims, 4 Drawing Sheets

PROCESS AND APPARATUS FOR THE COSMETIC TREATMENT OF ACNE VULGARIS

RELATED APPLICATION

This application is a continuation of application Ser. No. 09/204,593, filed Dec. 3, 1998, now U.S. Pat. No. 6,183,500.

TECHNICAL FIELD

This invention discloses a process for the cosmetic treatment of acne vulgaris by irradiation of the affected skin areas with light and an apparatus for the application of the process.

BACKGROUND ART

A known process uses UV light for the irradiation of the face. This, however, has the possible disadvantage of erythema formation or an undesirable oxidation of skin pigments.

Also known is a treatment with a cream containing approximately 0.5% benzoyl peroxide. The disadvantage of this treatment is possible skin dryness.

SUMMARY OF THE INVENTION

It is an object of the present invention to provide a process and an apparatus for the treatment of acne which not only eliminates the known disadvantages but also results in an excellent cosmetic effect.

DETAILED DESCRIPTION OF THE PREFERRED EMBODIMENTS(S)

Figure 1:
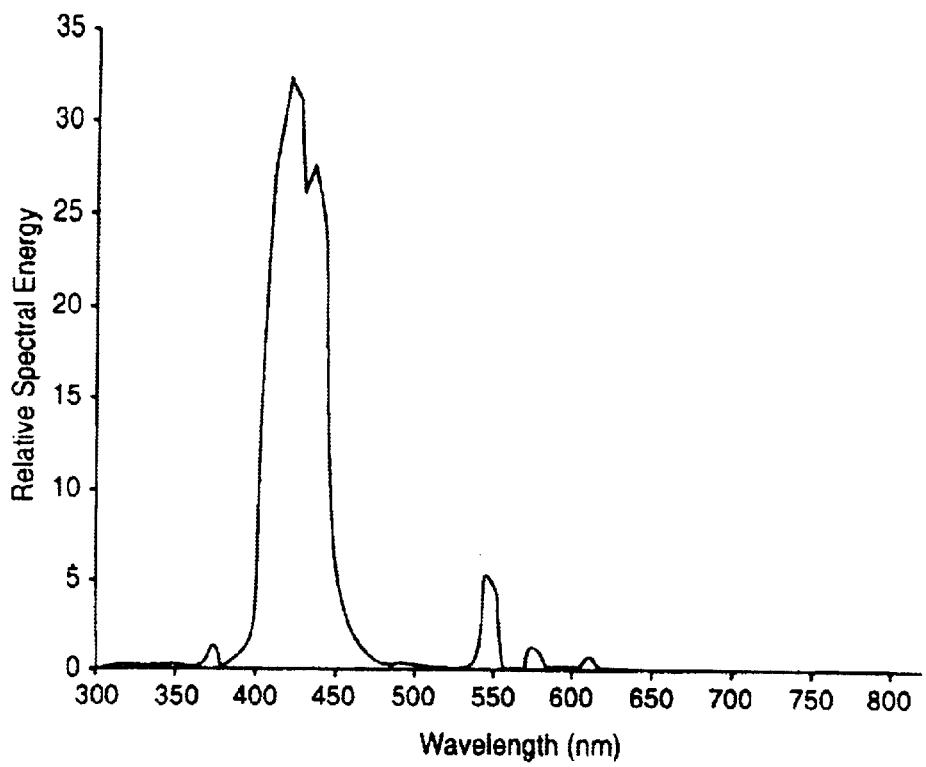
FIG. 1 shows the spectral energy distribution of a blue lamp according to the invention.
Figure 2:
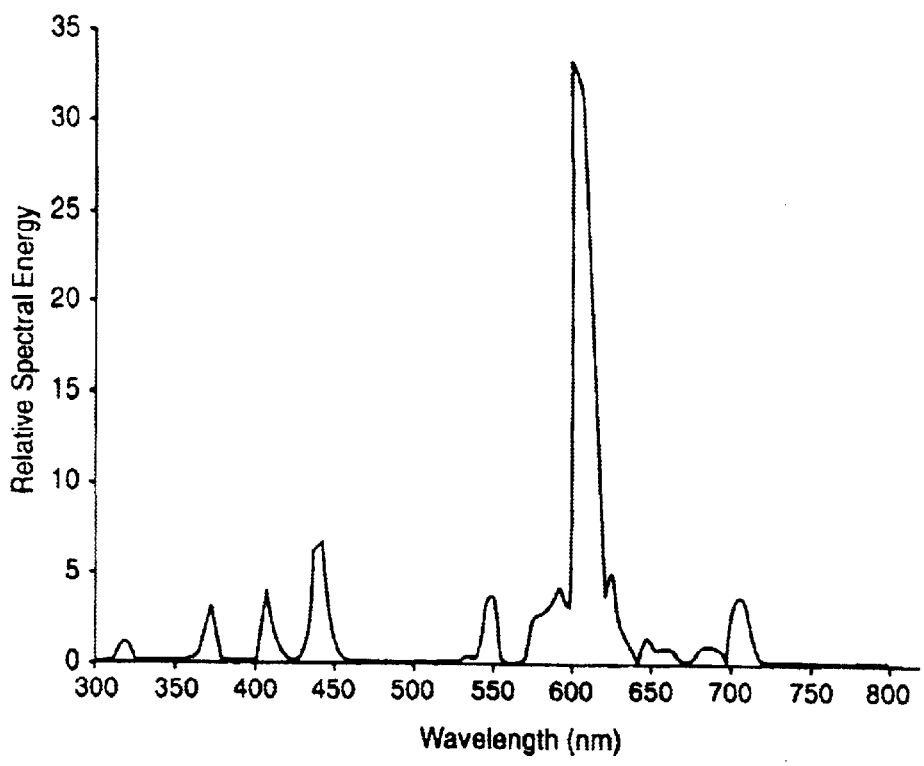
FIG. 2 shows the spectral energy distribution of a red lamp according to the invention.

This task is accomplished in accordance with the invention by applying light from low pressure mercury discharge (fluorescent) lamps having two different spectra, one in the blue range from 400 to 450 nm (FIG. 1), the other in the red range from 580 to 659 nm (FIG. 2).

Irradiation in accordance with the invention does not result in UV damage to the skin nor in significant skin dryness.

Figure 3:
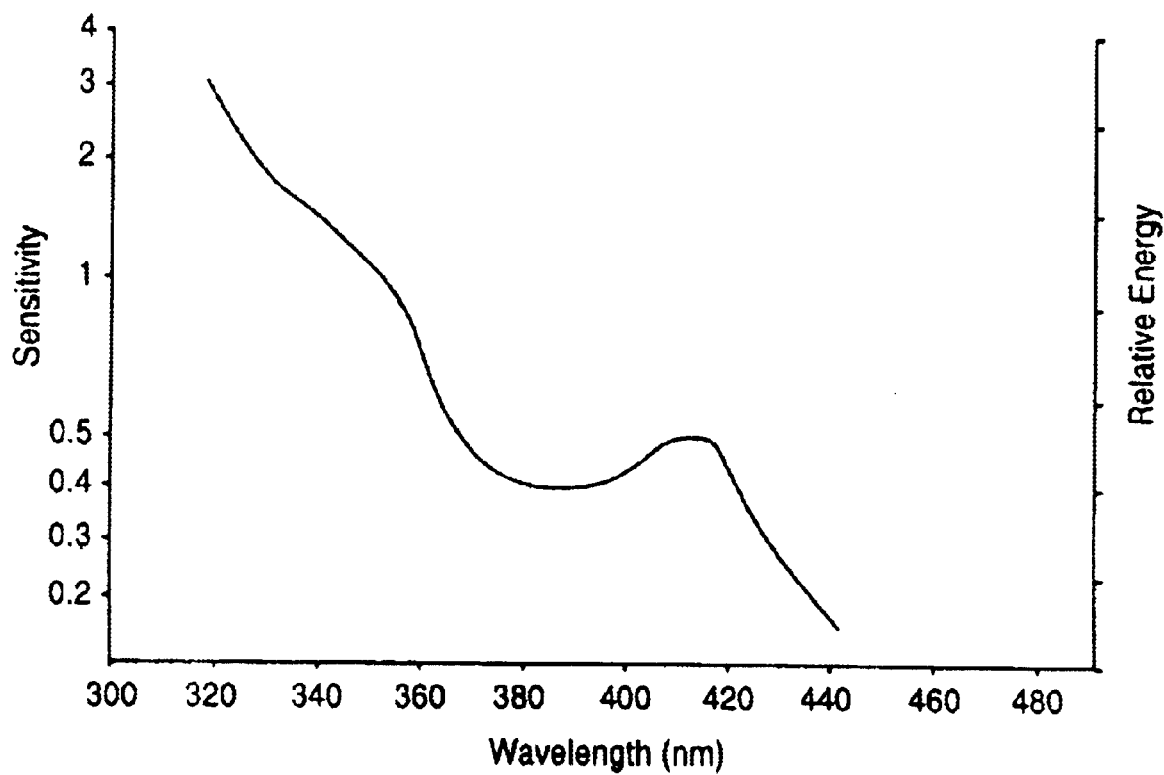
FIG. 3 shows the action spectrum for the inactivation of propionibacterium acne.

Both partial spectra in accordance with the present invention are additive. The resulting spectrum is adapted to the action spectrum for the inactivation of the propionibacterium acne (FIG. 3). It has a biostimulating effect on the skin cells. This is caused by the fact that propionibacterium acne produces porphyrins which may be excited by short wavelength light. This has a lethal effect on the bacteria.

Light exposure studies were conducted with 61 patients having mild to moderate acne. They were treated with blue-red light in accordance with the invention and with blue light. The results were compared with white light exposure and treatment with benzoyl peroxide cream.

Patients were instructed to use the lamps for 15 minutes each day or apply the benzoyl peroxide cream twice daily.

Patient assessment was conducted every four weeks. The results are shown in the following table:

|  | Blue/Red Light | | Blue Light | | White Light | | Cream | |
| --- | --- | --- | --- | --- | --- | --- | --- | --- |
| Observation | Doctor % | Patient % | Doctor % | Patient % | Doctor % | Patient % | Doctor % | Patient % |
| worse/unchanged | 27 | 27 | 25 | 50 | 46 | 46 | 19 | 19 |
| slight/moderate improvement | 18 | 27 | 42 | 33 | 46 | 46 | 44 | 50 |
| significant improvement | 55 | 46 | 33 | 17 | 8 | 8 | 37 | 31 |

The number listed under "doctor" refers to a doctor's assessment, the number in the "patient" column is the patient's assessment after blue light or cream treatment.

Results show that the best results were obtained with mixed blue/red light in accordance with the invention with an average reduction of 66% in inflammatory and 42% in non-inflammatory lesions. With blue light the reduction was 50% and 32%, with white light 21% and 0% and with benzoyl peroxide cream 61% and 58%, respectively.

Investigators assessment showed a significant improvement, 55% with blue/red light, 33% with blue light, 21% with white light and 37% with cream treatment.

Patients assessment showed a significant improvement of 46% with blue/red light, 16% with blue light, 8% with white light and 31% after cream treatment. After light exposure dryness was negligible.

Figure 4:
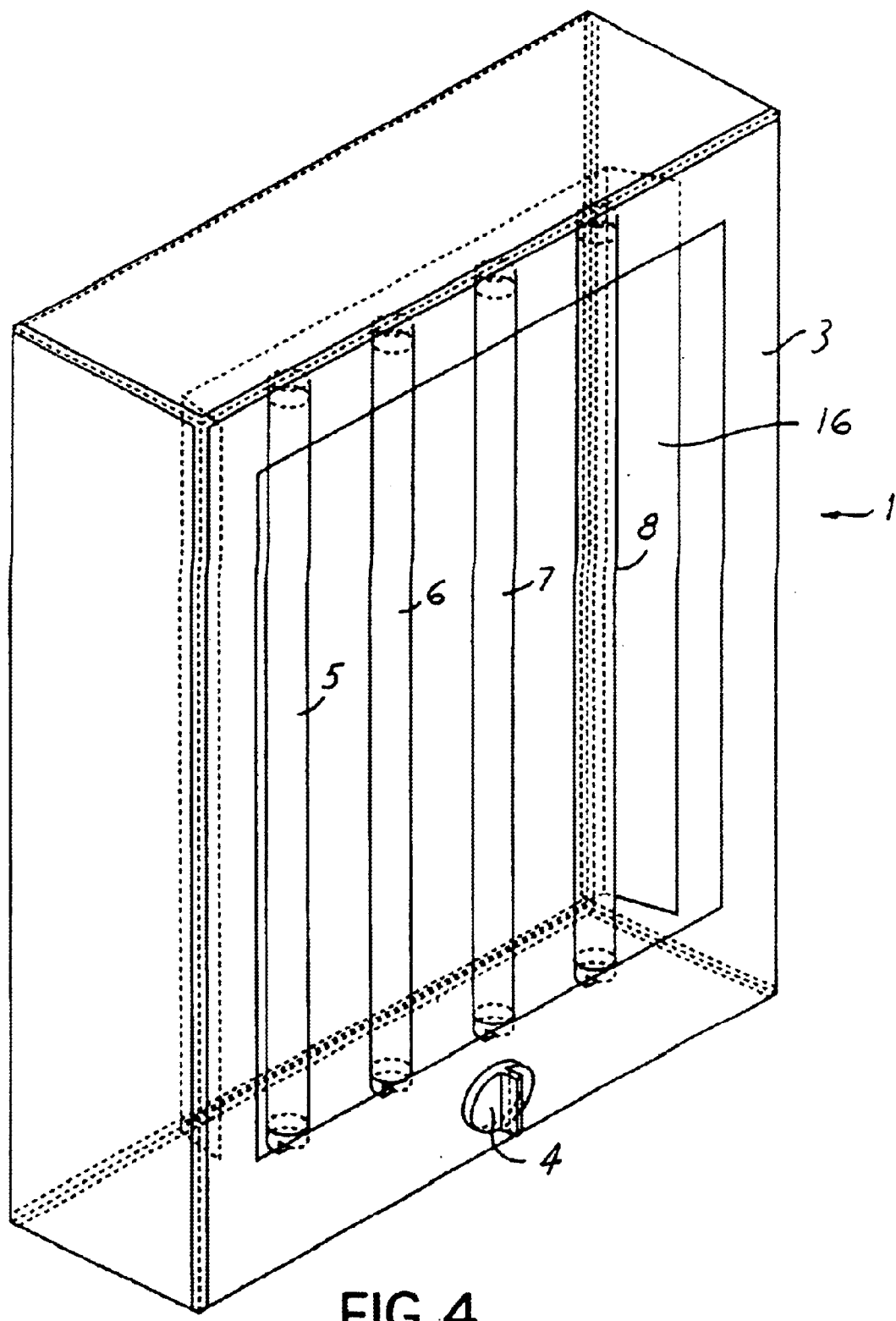
FIG. 4 shows an apparatus for the treatment of acne vulgaris in accordance with the invention including a housing 3, a timer switch 4, and double-ended fluorescent lamps 5, 6, 7, 8.

The apparatus 1 shown in FIG. 4 is provided with at least one blue and red lamp, each having a spectrum in accordance with FIG. 1 or 2, respectively. The lamps are of the double-ended low pressure mercury discharge (fluorescent) type, according to IEC Publication 60081. The embodiment in FIG. 4 shows four lamps 5, 6, 7, 8, arranged in parallel, having a bulb diameter of 15 to 40 mm and a length of 300 to 600 mm. Two of the lamps emit in the blue range, the other two in the red part of the spectrum. The arrangement of the lamps in the apparatus 1 is such that blue and red lamps alternate. In FIG. 4, lamps 5 and 7 have blue, lamps 6 and 8 red emission.

Figure 5:
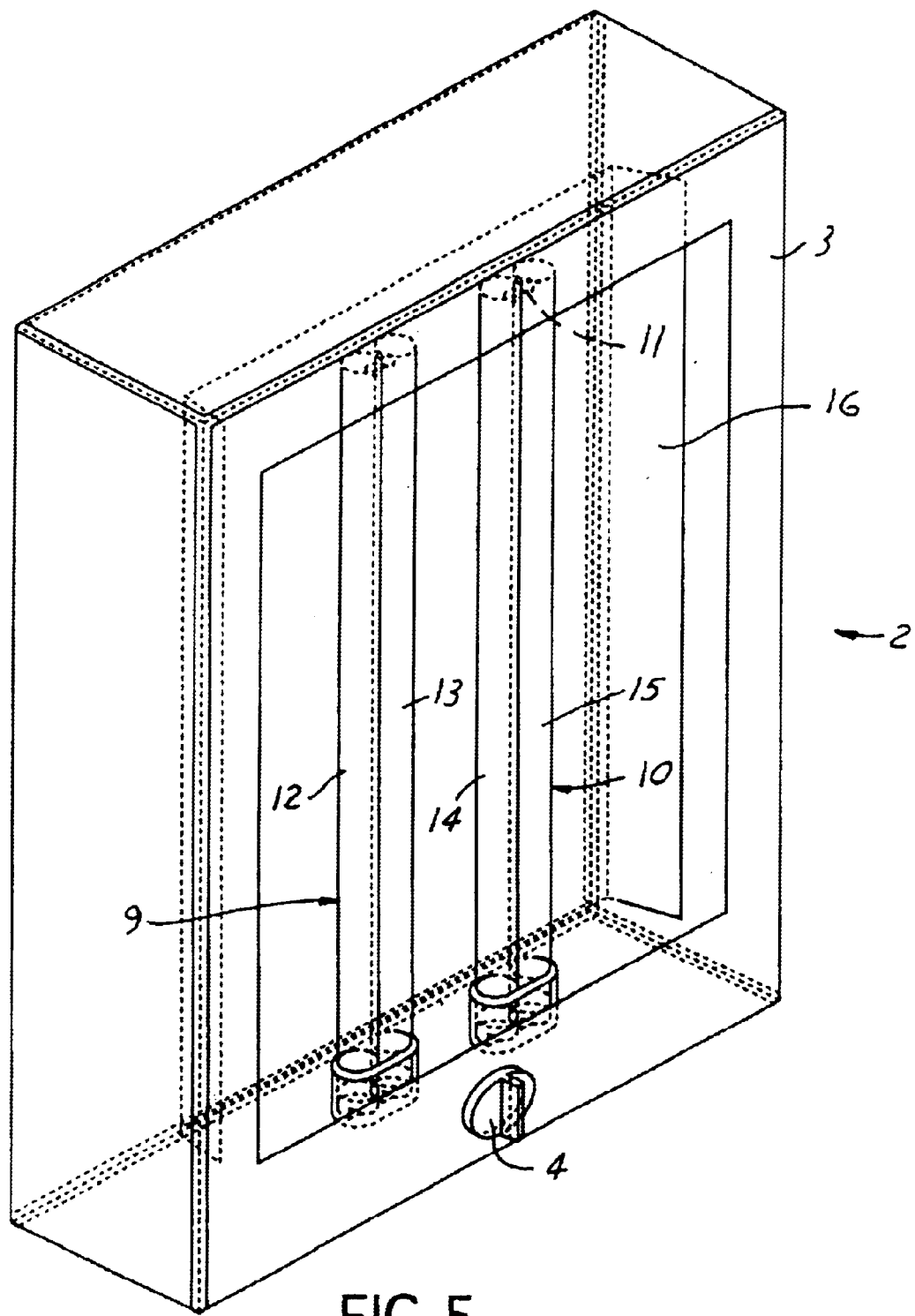
FIG. 5 shows an alternative embodiment of the apparatus shown in FIG. 4 which includes housing 3, timer switch 4, and single-ended fluorescent lamps 9, 10.

The embodiment of the apparatus 2 in FIG. 5 shows two single-ended fluorescent lamps 9, 10, according to IEC Publication 60901. Each lamp consists of two legs 12, 13 and 14, 15, which are joined together by means of a hollow glass tube 11 located opposite the base end, or by a U-bent tube sealed to both legs at the end opposite the base. The total length of each lamp is between 225 to 414 mm, one leg of each lamp is coated with blue, the other leg with red phosphor in accordance with the invention.

To increase the irradiation efficiency, an external reflector 16 is provided between each lamp and the housing 3 such that the light is preferentially emitted in the forward direction. Alternatively, two or more lamps are provided with a common reflector. Still another alternative is to apply the reflector as a reflective coating onto the inner bulb wall of a lamp between the glass and phosphor coating as an internal reflector.

Penetration depth of red light into the skin increases as from 600 nm up, depending also on the type of skin. Further, red light of longer wave lengths has a healing effect. To accommodate for this, variation of the intensity ratio of red to blue light can be advisable. Such accommodation in accordance with the invention can be effected by use of combinations of one blue with three red or one red with three blue lamps alternatively.

Each lamp can be operated on a dimmable ballast which allows for adjustment of the light intensity from 10 to 100% of the nominal value.

Blue light and also red light in the 615 to 655 nm region have been found to have a killing effect on propionibacterium acne within certain exposure times and red/blue intensity ratios.

What is claimed is:

1. A method for the cosmetic treatment of acne vulgaris, the method comprising:
    providing at least one single-ended fluorescent lamp having two legs, one leg emitting light in a blue region having an average wavelength from 400 to 450 nm and the other leg emitting light in a red region having an average wavelength from 580 to 659 nm; and
    simultaneously irradiating affected skin areas with both legs of the at least one lamp.

2. The method according to claim 1, wherein the red region has an average wavelength from 580 to 630 nm.

3. The method according to claim 1, wherein the red region has an average wavelength from 630 to 658 nm.

4. The method according to claim 1, wherein the red region has an average wavelength from 615 to 655 nm.

5. The method according to claim 1, wherein the irradiating step is conducted once per day for about 15 minutes.

6. An apparatus for the cosmetic treatment of acne vulgaris, the apparatus comprising:
    a housing; and
    at least one single-ended fluorescent lamp disposed within the housing, the at least one lamp having two legs for simultaneously irradiating affected skin areas with light characterized by a combination of two emission spectra, wherein one leg emits light in a blue region having an average wavelength from 400 to 450 nm and the other leg emits light in a red region having an average wavelength from 580 to 659 nm.

7. The apparatus according to claim 6, wherein the at least one lamp includes two single-ended fluorescent lamps, each lamp having two legs which are joined together by a tube.

8. The apparatus according to claim 7, wherein the lamps are arranged such that the legs emitting light in the blue region and the legs emitting light in the red region alternate.

9. The apparatus according to claim 7, wherein one lamp has two legs that both emit light in one of the blue region and the red region, and the other lamp has one leg that emits light in the blue region and another leg that emits light in the red region.

10. The apparatus according to claim 6, wherein the at least one lamp has a length of approximately 225 to 414 mm.

11. The apparatus according to claim 6, further comprising at least one reflector arranged between each lamp and the housing for increasing the irradiation efficiency.

12. The apparatus according to claim 11, wherein the at least one reflector includes a reflective coating provided on an inner bulb wall of each lamp.

13. The apparatus according to claim 6, further comprising a timer switch in communication with the at least one lamp for limiting the exposure time of affected skin areas to irradiation.

14. The apparatus according to claim 6, wherein the at least one lamp is operated on a dimmable ballast to allow for adjustment of a light intensity of the lamp.

15. A method for the cosmetic treatment of acne vulgaris, the method comprising:
    providing at least four double-ended fluorescent lamps, the lamps providing light characterized by a combination of two emission spectra, one in a blue region having an average wavelength from 400 to 450 nm and the other in a red region having an average wavelength from 580 to 659 nm; and
    irradiating affected skin areas using the lamps.

16. An apparatus for the cosmetic treatment of acne vulgaris, the apparatus comprising:
    a housing; and
    at least four double-ended fluorescent lamps disposed within the housing, the lamps for irradiating affected skin areas with light characterized by a combination of two emission spectra, one in a blue region having an average wavelength from 400 to 450 nm and the other in a red region having an average wavelength from 580 to 659 nm.

17. The apparatus according to claim 16, wherein the at least four lamps have a bulb diameter of approximately 15 to 40 mm and a length of approximately 300 to 600 mm.

18. The apparatus according to claim 16, wherein a first two of the at least four lamps emits light in the blue region and a second two of the at least four lamps emits light in the red region.

19. The apparatus according to claim 16, wherein one of the at least four lamps emits light in one of the blue region and the red region, and three of the at least four lamps emit light in the other of the blue region and the red region.

20. The apparatus according to claim 16, wherein the lamps are arranged substantially parallel to each other.

21. The apparatus according to claim 16, further comprising at least one reflector arranged between each lamp and the housing for increasing the irradiation efficiency.

22. The apparatus according to claim 21, wherein the at least one reflector includes a reflective coating provided on an inner bulb wall of each lamp.

23. The apparatus according to claim 16, further comprising a timer switch in communication with the lamps for limiting the exposure time of affected skin areas to irradiation.

24. The apparatus according to claim 16, wherein the lamps are operated on a dimmable ballast to allow for adjustment of a light intensity of the lamps.

25. An apparatus for the cosmetic treatment of acne vulgaris, the apparatus comprising:
    a housing; and
    at least two single-ended fluorescent lamps disposed within the housing, each lamp having two legs, the at least two lamps for irradiating affected skin areas with light characterized by a combination of two emission spectra, one leg of each lamp emitting light in a blue region having an average wavelength from 400 to 450 nm and the other leg of each lamp emitting light in a red region having an average wavelength from 580 to 659 nm wherein the lamps are operated on a dimmable ballast to allow for adjustment of a light intensity of the lamps.

26. An apparatus for the cosmetic treatment of acne vulgaris, the apparatus comprising:

a housing;

at least two lamps disposed within the housing, the at least two lamps for irradiating affected skin areas with light characterized by a combination of two emission spectra, one in a blue region having an average wavelength from 400 to 450 nm and the other in a red region having an average wavelength from 580 to 659 nm; and a timer in communication with the lamps for limiting the operating time of the lamps.

* * * * *